US010532070B2

(12) United States Patent
Gregory et al.

(10) Patent No.: US 10,532,070 B2
(45) Date of Patent: Jan. 14, 2020

(54) ANTIVIRAL COMPOSITION AND APPLICATIONS OF IRON-DOPED APATITE NANOPARTICLES

(71) Applicants: Jessica M. Gregory, Butte, MT (US); Jack L. Skinner, Butte, MT (US); Marisa L. Pedulla, Helena, MT (US); M. Katie Hailer, Butte, MT (US)

(72) Inventors: Jessica M. Gregory, Butte, MT (US); Jack L. Skinner, Butte, MT (US); Marisa L. Pedulla, Helena, MT (US); M. Katie Hailer, Butte, MT (US)

( * ) Notice: Subject to any disclaimer, the term of this patent is extended or adjusted under 35 U.S.C. 154(b) by 0 days.

(21) Appl. No.: 15/902,272

(22) Filed: Feb. 22, 2018

(65) Prior Publication Data

US 2019/0255105 A1 Aug. 22, 2019

(51) Int. Cl.
*A61K 9/51* (2006.01)
*A61K 9/00* (2006.01)
(Continued)

(52) U.S. Cl.
CPC ............ *A61K 33/42* (2013.01); *A61K 9/0021* (2013.01); *A61K 9/0053* (2013.01); (Continued)

(58) Field of Classification Search
None
See application file for complete search history.

(56) References Cited

PUBLICATIONS

JM Andriolo, RR Rossi, CA McConnell, BI Connors, KL Trout, K Hailer, ML Pedulla, JL Skinner. "Influence of Iron-Doped Apatite Nanoparticles on Viral Infection Examined in Bacterial Versus Algal Systems." IEEE Transactions on Nanobioscience, vol. 15 No. 8, Dec. 2016, pp. 908-916. (Year: 2016).*

(Continued)

*Primary Examiner* — Isaac Shomer
(74) *Attorney, Agent, or Firm* — Mitchell J. W. Vap

(57) ABSTRACT

Iron-doped apatite nanoparticles (IDANPs) are useful for the prevention, treatment, or alleviation of signs or symptoms associated with viral activation or infection. IDANPs have demonstrated a significant influence over herpes simplex virus 1 (HSV-1) infection of two mammalian cell lines. Specifically, IDANPs decreased HSV-1 infection of African Green Monkey kidney epithelial (Vero) cells by 84% and HSV-1 infection of human lung bronchus (BEAS-2B) cells by 71%. IDANPs consist of hydroxyapatite (HA) doped with iron. HA is a mineral known to be biocompatible and analogous to the inorganic constituent of mammalian bone and teeth and has been approved by the Food and Drug Administration (FDA) for many applications in medicine and dentistry. Lactate Dehydrogenase (LDH) and XTT (2,3-Bis 2-methoxy-4-nitro-5-sulfophenyl-2H-tetrazolium-5-carboxanilide inner salt) cytotoxicity assays revealed that IDANPs are largely non-toxic to Vero, BEAS-2B, and human cervical cancer (HeLa) cells lines. HSV-1 afflicted individuals in the United States have been estimated as high as ⅔ the population. Because IDANPs dramatically decrease HSV-1 infection and are largely non-toxic, their application as an antiviral agent is evident. Further, although iron(III) alone has been shown to diminish replication of deoxyribonucleic acid (DNA)- and ribonucleic acid (RNA)-containing viruses, IDANP cytotoxicity studies indicate that encasement and delivery of iron within an apatite unit cell structure diminishes significantly, and in some cases eliminates, cytotoxicity posed by the introduction of iron(III) alone.

13 Claims, 6 Drawing Sheets
(6 of 6 Drawing Sheet(s) Filed in Color)

(51) Int. Cl.
*A61K 33/42* (2006.01)
*A61P 31/22* (2006.01)

(52) U.S. Cl.
CPC ............ *A61K 9/5115* (2013.01); *A61P 31/22* (2018.01); *Y10S 977/773* (2013.01); *Y10S 977/906* (2013.01)

(56) References Cited

PUBLICATIONS

JM Andriolo, RM Hensleigh, CA McConnell, M Pedulla, K Hailer, R Kasinath, G Wyss, W Gleason, JL Skinner. "Iron-doped apatite nanoparticles for improvement of phage therapy." Journal of Vacuum Science and Technology B, vol. 32(6), Nov./Dec. 2014, pp. 06FD01-1 to 06FD01-7. (Year: 2014).*

JM Gregory. "Doped Apatite Nanoparticles: Characterization and Biomedical Relevance." University of Montana Thesis—Abstract Only. https://scholarworks.umt.edu/etd/10963/ accessed Jun. 21, 2018, published 2017, 2 printed pages. (Year: 2017).*

JM Andriolo, GF Wyss, JP Murphy, ML Pedulla, MK Hailer, JL Skinner. "Iron-Doped Apatite Nanoparticles Delivered via Electrospun Fiber Mesh for Maximized Bacterial Killing by Bacteriophage." Materials Research Society Advances, 2017, pp. 2465-2470. (Year: 2017).*

* cited by examiner

ANTIVIRAL COMPOSITION AND APPLICATIONS OF IRON-DOPED APATITE NANOPARTICLES

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

Compositions of Iron-Doped Apatite Nanoparticles (IDANP's) herein described, dramatically decrease viral infection, and are largely non-toxic. As such, IDANP's are useful for the prevention, treatment, or alleviation of signs or symptoms associated with viral activation or infection. The nanoparticles (NPs) used in this research are composed of hydroxyapatite (HA) $Ca_{10}(PO_4)_6(OH)_2$, doped with iron. HA, which is a constituent of mammalian bones and teeth, has been extensively studied and approved by the Food and Drug Administration (FDA) for applications in medicine and dentistry (Palmer et al., *Chemical Reviews,* 2008 & Hench, *Journal of the American Ceramic Society,* 1998).

In a publication by Felix d'Herelle in 1931, viruses which specifically kill bacteria were used to treat acute bacterial infection (d'Herelle, *Bulletin of the New York Academy of Medicine,* 1931). These viruses were termed bacteriophage (phage) by d'Herelle, and treatment of bacterial infection by phage has since been referred to as phage therapy. However, the discovery and use of traditional antibiotics such as penicillin (Fleming, *British Journal of Experimental Pathology,* 1929) de-emphasized wide spread use of phage therapy. In 2013, the Centers for Disease Control and Prevention estimated that each year, 2 million people in the United States become infected with antibiotic-resistant bacteria, of which, approximately 23,000 die as a direct result of such infections (2013). Rapid bacterial resistance to traditional antibiotics therefore calls for alternative therapies such as phage therapy to be revisited. Previous research has shown that addition of IDANPs to bacteria prior to phage exposure results in increased bacterial plaques in vitro (Andriolo et al., *Journal of Vacuum Science and Technology B,* 2013). Because IDANPs enhance phage killing of bacteria, initial interest in their study as an adjuvant to phage therapy was garnered.

Bacterial viruses (phage) and human viruses have many similarities including structure and mechanism of infection. To ensure safety of IDANPs in a human system, it had to be established that while these nanoparticles (NPs) increased phage infection and killing of bacterial cells, that IDANPs did not also increase eukaryotic virus infections and killing of eukaryotic cells. To test IDANP-effect on eukaryotic virus infection of eukaryotic cells, experiments were carried out using *Chlorella variabilis* NC64A (NC64A) and its virus, Paramecium bursaria chlorella virus 1 (PBCV-1) (Andriolo et al., *IEEE Transactions on Nanobioscience,* 2016). Results indicated that in an algal system, viral infections were not increased or decreased by the addition of IDANPs.

Previous work has shown iron(III) inactivates HSV-1 (Sagripanti et al., *Applied and Environmental Microbiology,* 1993), and in more recent studies, it has been shown that iron(III) inhibits replication of DNA and RNA viruses (Terpilowska et al., *Biometals,* 2017). However, specific therapeutic applications of IDANPs regarding viral infection have previously not been disclosed or studied. The IDANP compositions and methods of use herein described, dramatically decrease viral infection, and are largely non-toxic to mammalian cells. As such, IDANP's are useful for the prevention, treatment, or alleviation of signs or symptoms associated with viral activation or infection.

BRIEF SUMMARY OF THE INVENTION

IDANP effect on viral infection of African Green Monkey kidney epithelial cells (Vero) and human lung bronchus cells (BEAS-2B) was investigated. The virus used for testing was herpes simplex virus 1 (HSV-1). Investigations revealed that IDANP influence over HSV-1 infection of Vero and BEAS-2B cells was significant ($p<0.001$). IDANPs decreased HSV-1 infection of Vero cells by 84%, and HSV-1 infection of BEAS-2B cells by 71%.

IDANPs used in this research are composed of HA doped with iron. HA is a constituent of mammalian bones and teeth and has been extensively studied and approved for medical and dental applications by the FDA (Palmer et al., *Chemical Reviews,* 2008 & Hench, *Journal of the American Ceramic Society,* 1998). To establish the doping of HA with iron would not diminish biocompatibility, cytotoxicity evaluations were performed on IDANPs. The first cytotoxicity test used measured cell distress by lactate dehydrogenase (LDH) release, and the second, measured cell health by oxidoreductase enzyme activity. Results showed minimal to no increase in LDH release by three cell lines: 0.00% in BEAS-2B and human cervical cancer (HeLa) cell lines, and 4.27% in Vero cell line. IDANP effect on cell health was evaluated by XTT (2,3-Bis 2-methoxy-4-nitro-5-sulfophenyl-2H-tetrazolium-5-carboxanilide inner salt) cytotoxicity assay. XTT assays revealed no significant difference in oxidoreductase enzyme activity in Vero ($p=0.276$), BEAS-2B ($p=0.131$), or HeLa ($p=0.960$) cell lines. An alternative test to XTT cytotoxicity assay is an MTT (3-(4,5-dimethylthiazol-2-yl)-2,5-diphenyltetrazolium bromide) cytotoxicity assay. Both tests involve the reduction of tetrazolium salts (XTT or MTT) to formazan by oxidoreductase enzymes released by cells and are good indicators of cell health. Previous researchers showed that iron(III) ions alone inhibit replication of DNA and RNA viruses (Terpilowska et al., *Biometals,* 2017). However, using the MTT assay, these researchers also showed that 150 μM iron(III) (as is found in IDANPs), caused a reduction in cell viability of HEp-2 (HeLa contaminant) cells to ~73%. For comparison, at the same concentration, IDANPs maintain 100% cell viability in Vero and HeLa cell lines, and 94.6% in the BEAS-2B cell line. Therefore, IDANPs provide a biocompatible method for iron delivery to act as an effective and safe anti-viral agent.

IDANPs are synthesized using wet chemical precipitation methods (Andriolo et al., *Journal of Vacuum Science and Technology B,* 2013 & Andriolo et al., *IEEE Transactions on

*Nanobioscience,* 2016). Synthesis of IDANPs involves iron replacement of calcium in the apatite unit cell to 30% iron in the molar ratio of total iron plus calcium. Citrate was used as a capping agent to arrest NPs at the nanoscale. The reaction formula is as follows:

7Ca(OH)2+3FeCl3+6KH2PO4 Citric Acid Ca7Fe3 (PO4)6(OH)2+6KOH+12H2O+9Cl—

During synthesis of 30% IDANPs with 1× citrate, a 500 mL flask held at 25° C. was filled with 200 mL deionized water and stirred by stir bar as the following reagents were added in the order listed:

- 0.260 g Calcium Hydroxide (Ca(OH)2)
- 0.243 g Iron Chloride (FeCl3)
- 0.263 g Citric Acid Anhydrous (C6H7O7)
- 0.408 g monopotassium phosphate (KH2PO4) that was pre-dissolved in 50 mL deionized water is added drop-wise over a period of 1 minute.

The final solution was measured at a pH of approximately 4.5 and brought up to a pH of 7.5 using 1 M NaOH. IDANPs were then stirred at 25° C. for seven days. After seven days, IDANPs were centrifuged for 30 min at 2000 rpm. IDANP supernatant was then removed, leaving the IDANP pellet. The pellet was washed 2× with sterile, deionized water (18 MΩ), and IDANPs were re-suspended in deionized water before being sterilized in an autoclave for 40 minutes. IDANP concentration resulting from this synthesis procedure was estimated to be 1.54 mg/mL by simple drying method and weighing of dried IDANPs.

Original cell cultures were maintained at 37° C. and 5% carbon dioxide in 75 cm2 flasks. Original cultures were grown in minimal essential media (MEM) with 10% fetal bovine serum (FBS) and 1% penicillin-streptomycin (P-S) antibiotic.

To evaluate IDANP influence over HSV-1 infection of Vero and BEAS-2B cells, plaque assays were used. HSV-1 maintenance and storage and plaque assay methods were adapted from Blaho et al., *Current Protocols in Microbiology,* 2005. When original cultures were confluent, Vero and BEAS-2B cells maintained in 75 $cm^2$ flasks were lifted with trypsin (0.25%)-EDTA and split into 25 $cm^2$ flasks (15-17,000 cells per flask counted directly by hemocytometer) for plaque assay. In 25 $cm^2$ flasks, Vero and BEAS-2B cells were grown in MEM with 5% FBS and 1% P-S for 3-4 days, or until confluent. On the day of plaque assay, HSV-1 was removed from −80° C. freezer and thawed in the biosafety hood. Once thawed completely, HSV-1 was diluted into 199V media (Blaho et al., *Current Protocols in Microbiology,* 2005), or 199V with suspended IDANPs (1.54 mg/mL) to a pre-determined concentration for countable plaques (~50-100 PFUs/mL). To prepare 199V media with suspended IDANPs ($199V^{NP}$), IDANPs were centrifuged and supernatant removed before IDANPs were re-suspended in 199V. Growth media was then aspirated from 25 $cm^2$ flasks and replaced with 1 mL of HSV-1 in 199V or HSV-1 in $199V^{NP}$. HSV-1 was allowed to adsorb to the cells for 2 hr in an incubator (37° C., 5% CO2) with gentle rocking every 30 min. After the 2 hr adsorption period, 199V or $199V^{NP}$ was removed from the flasks and replaced with 3 mL MEM with 7.5 μg/mL pooled human immunoglobulin (IgG). Flasks were then incubated for 3 days at 37° C. with 5% $CO_2$. After 3 days, media was removed from the 25 $cm^2$ flasks. To each flask, 1 mL methanol was added and left in ambient conditions for 5 min. After 5 min, methanol was removed from the flasks and replaced with 2 mL KaryoMax Giemsa Stain (diluted 1:10 with distilled water). Cell monolayers were stained for 20 min before the stain was removed and cell monolayers were rinsed with deionized water. Plaques were subsequently enumerated. Plaque assay was repeated in three separate experiments, with four, five, and seven pseudo-replicates per treatment condition for Vero cell line, and three, six, and seven for the BEAS-2B cell line. Negative controls were performed in all experiments, in which 199V or $199V^{NP}$ without HSV-1 were exposed to the cell lines during the 2 hr infection period. Negative control flasks all revealed no plaques, ensuring plaque formation was due to the addition of HSV-1 to the mammalian cell lines.

For LDH cytotoxicity assay, original, confluentcultures of Vero, BEAS-2B, or HeLa were subject to lifting by 5 mL trypsin (0.25%)-EDTA before being pelleted by centrifugation (3000 rpm, 5 min) and trypsin subsequently replaced with MEM (10% FBS, 1% P-S). Cells were counted directly by hemocytometer and plated in a 96-well plate (7,000-9,000 cells per well) in 100 μL MEM (10% FBS, 1% P-S) and grown to confluence over the next 1-2 days. After cells were confluent, MEM was removed from the wells and replaced with either: (1) fresh MEM (10 wells), (2) fresh MEM with suspended IDANPs (25° C., 30% Fe, 5.5 mM citrate at 1.54 mg/mL, 10 wells), or Dulbecco's phosphate buffered saline (DPBS, 2 wells) as a vehicle control. The three treatments used were applied to the cell monolayers for 24 hr. Approximately 1 hr before the end of treatment time, cytotoxicity kit reagents were prepared according to protocols distributed by Biovision for Colorimetric Assay II (Documentation can be found at https://www.biovision.com/documentation/datasheets/K313.pdf). Approximately 15 min before the end of treatment time, 10 μL of prepared cell lysis solution was added to five of the MEM-only wells and pipetted up and down. The five wells inoculated with cell lysis solution constituted the high control for LDH cytotoxicity evaluation. After treatment time, solution from each of the wells was collected and placed in microcentrifuge tubes. Microcentrifuge tubes were spun at 600 rgf for 5 min to pellet and remove any large cell components and IDANPs. After centrifugation and removal of the pelleted material, 10 μL from each microcentrifuge tube was transferred to individual wells in a fresh 96-well plate. To each well, 100 μl LDH Reaction Mix was added, pipetted up and down to mix, and incubated (37° C.) in the UV-Vis spectrometer for 1 hr 15 min with constant monitoring every 3 min at 450 nm. Biovision protocols indicated the reading should be taken when the high control was ~2.0 and the low control was <0.8. Wells with cell monolayers treated with NPs were repeated in 10 wells, low and high controls were repeated in five replicate wells each, and vehicle controls were performed in duplicate. Reference was taken after analysis period by taking additional readings at 450 nm and 620 nm simultaneously. Cytotoxicity (%) was determined by the following formula provided by Biovision (Documentation can be found at https://www.biovision.com/documentation/datasheets/K313.pdf):

$$\text{Cytotoxicity (\%)}=[((\text{Test Sample}-\text{Low Control}))/((\text{High Control}-\text{Low Control}))]\times 100\%$$

Using cytotoxicity (%), it was determined that IDANPs posed 0.00% cytotoxicity to BEAS-2B and HeLa cell lines, and 4.27% cytotoxicity to the Vero cell line.

For XTT cytotoxicity evaluation, original cultures of Vero, BEAS-2B, and HeLa were subject to lifting by 5 mL trypsin (0.25%)-EDTA before being pelleted by centrifugation (3000 rpm, 5 min), and trypsin was subsequently replaced with MEM (10% FBS, 1% P-S). Cells were counted directly by hemocytometer and plated in a 96-well plate (7,000-9,000 cells per well) in 100 μL=MEM (10% FBS, 1% P-S) and grown to confluence over the next 1-2 days. After cells were confluent, MEM was removed from the wells and replaced with either: (1) fresh MEM (11 wells), (2) fresh MEM with suspended IDANPs (25° C., 30% Fe, 5.5 mM citrate at 1.54 mg/mL, 11 wells), DPBS (2 wells) as a vehicle control. Treatments were applied to cell monolayers for 24 hr. During the last hour of exposure to the treatments, XTT was dissolved 0.01 g into 10 mL DPBS, and phenazine methosulfate (PMS) was dissolved 0.05 g into 1 mL sterile, deionized water (18 MΩ). Then, 100 μl, PMS solution was pipetted into 5 mL of the XTT solution. During preparation, all of these solutions were kept on ice. In addition, 10 μL cell lysis solution was added to one well containing MEM only, and one well containing MEM with suspended IDANPs as dead controls. At the conclusion of treatment, all solution was removed from the wells, cell monolayers were washed 2× with DPBS, and replaced with fresh MEM. This wash/replacement procedure was used to eliminate any signal coming from XTT interacting with IDANPs or IDANPs alone. Each well was subsequently inoculated with 100 μL XTT/PMS solution, and plates were placed back into the incubator for 2 hrs, with final absorption read at 450 nm (reference at 620 nm). During these studies, 10 replicate wells were treated with MEM only, ten with MEM with suspended IDANPs, two dead controls (one per MEM or MEM with IDANPs) were used, as well as two vehicle controls (treated with DPBS). Using a one way ANOVA in SigmaPlot (V.11) to analyze XTT results, no significant difference in mitochondrial enzyme activity was observed between Vero ($p=0.276$), BEAS-2B ($p=0.131$), or HeLa ($p=0.960$) cells which had or had not been exposed to IDANPs.

Where necessary, significance of results were determined in SigmaPlot using a one way ANOVA V.11.

IDANPs have demonstrated a significant influence over HSV-1 infection of two mammalian cell lines. Specifically, IDANPs decreased HSV-1 infection of Vero cells by 84% and HSV-1 infection of BEAS-2B cells by 71%. LDH and XTT cytotoxicity assays revealed that IDANPs are largely non-toxic to Vero, BEAS-2B, and HeLa cells lines. Because IDANPs dramatically decrease HSV-1 infection and are largely non-toxic, their application as an antiviral agent is evident. Further, although iron(III) alone has been shown to diminish replication of DNA and RNA viruses (Terpilowska et al., *Biometals,* 2017), IDANP cytotoxicity studies indicate that encasement and delivery of iron within an apatite unit cell structure diminishes significantly, and in some cases eliminates, cytotoxicity posed by the introduction of iron (III) alone. As such, compositions and methods of using IDANPs for the prevention, treatment, or alleviation of signs or symptoms associated with viral activation or infection are disclosed herein. The compositions of this invention include IDANPs suspended in one of the following, but are not limited to the following: solid, semi-solid, Newtonian or Non-Newtonian fluid, or powder. One skilled in the art would recognize that such compositions could be delivered by various therapeutic means including, but not limited to injection, oral administration, or direct application.

IDANP compositions used for prevention, treatment, or alleviation of signs or symptoms associated with viral activation or infection are prepared as follows: IDANPs are synthesized as stated herein (see [0007] and [0026]). Supernatant created during IDANP synthesis/preparation is removed by some method, for example, centrifugation of the particles and removal of supernatant by pipette. IDANPs without supernatant are then suspended by any means suitable into any solid, semi-solid, Newtonian or Non-Newtonian fluid, or powder by mixing. One example would include simply mixing synthesized IDANPs into these materials by stir bar on a stir plate, or vortexing.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Virus Maintenance and Cell Culture.

Figure 1:
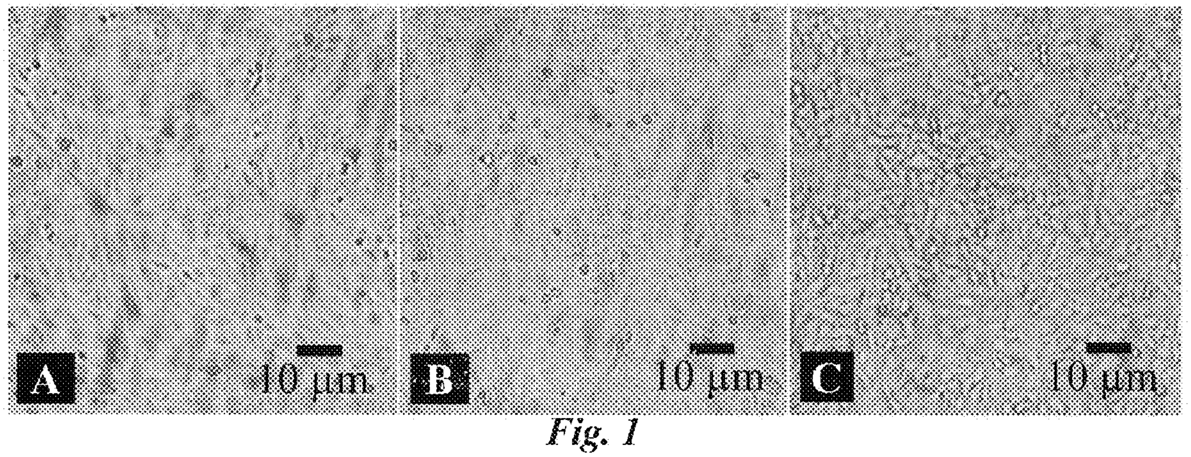
FIG. 1 Microscope images of confluent A Vero, B BEAS-2B, and C HeLa cells. Cells were grown in at 5% $CO_2$ in 75 $cm^2$ flasks containing 23-25 mL MEM supplemented with 10% FBS and 1% P-S. To maintain healthy cultures, cell media was changed every 3-4 days, and confluent cultures were lifted with trypsin (0.25%)-EDTA and split by removing all but 1 mL of the original cell culture, before being placed back in the incubator with fresh media.

HSV-1 virus stock was prepared and stored as previously described (Blaho et al., *Current Protocols in Microbiology,* 2005) and thawed (from −80° C.) just prior to being added to Vero or BEAS-2B cells for infection. Vero, BEAS-2B, and HeLa cell lines were maintained in an incubator (7° C., 5% $CO_2$) in 75 $cm^2$ flasks with minimal essential media (MEM) supplemented with 10% fetal bovine serum (FBS) and 1% penicillin-streptomycin antibiotic (P-S). To maintain healthy cultures, cell media was changed every 3-4 days, and confluent cultures (FIG. 1) were lifted with trypsin (0.25%)-EDTA and split by removing all but 1 mL of the original cell culture, before being placed back in the incubator with fresh media.

IDANP Synthesis.

Figure 2:
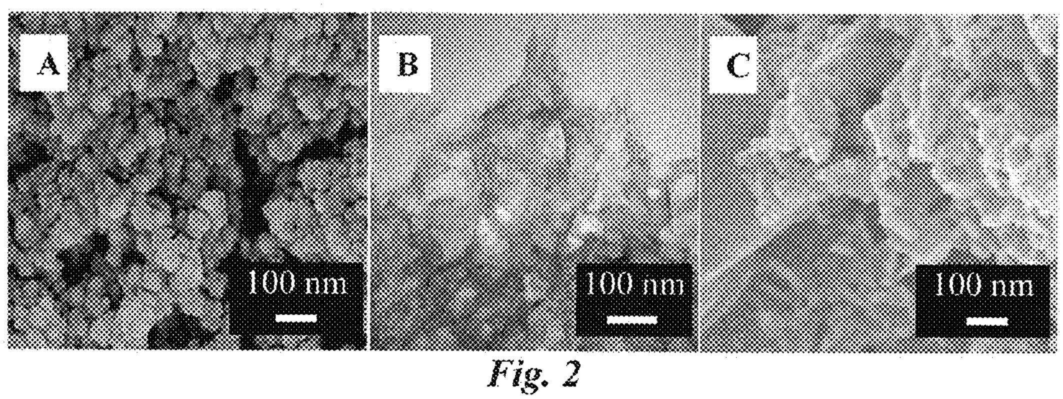
FIG. 2 Electron micrographs of IDANPs synthesized under different conditions. A Scanning electron micrograph of IDANPs synthesized at 25° C., with 30% iron-doping, and 5.5 mM citrate. IDANPs show spherical morphology with particle diameters ranging from 20-50 nm. B Transmission electron micrograph showing IDANPs synthesized at 25° C., with no iron or citrate. Apatite nanoparticles made in this way revealed shard or broken glass-like morphology. C Scanning electron micrograph of IDANPs synthesized at 25° C., with 30% iron-doping, and no citrate. Lack of citrate during preparation resulted in IDANP elongation.

Synthesis of IDANPs has been described previously (Andriolo et al., *Journal of Vacuum Science and Technology B,* 2013 & Andriolo et al., *IEEE Transactions on Nanobioscience,* 2016). IDANPs resemble HA, a mineral that is well known to be biocompatible and most analogous to the inorganic constituent of mammalian bone and teeth (Palmer et al., *Chemical Reviews,* 2008). Such properties allow these NPs to serve as biocompatible adjuvants capable of entering a physiological system without significant immune system rejection. Previous synthesis investigations have accomplished the synthesis of citrate functionalized and/or dispersed IDANPs (FIG. 2A). The citrate ions complex with $Ca^{2+}$, and mediate the reaction leading to the formation of nanoapatite particles. The carboxylates of citrate, which at physiological pH are deprotonated, give rise to Coulombic repulsion in adjacent NPs. This repulsion causes dispersion and colloid formation. During synthesis, it was assumed that iron replaces calcium in the apatite unit cell to 30% iron in the ratio of total iron plus calcium. Lack of iron during synthesis results in elongated glass-like morphology of the particles (FIG. 2B). Citrate was used as a capping agent to arrest NPs at the nanoscale. Lack of citrate results in extended particle growth which resembles longer chains (FIG. 2C). The theoretical reaction formula is as follows:

$$7Ca(OH)2 + 3FeCl3 + 6KH2PO4 \xrightarrow{\text{Citric Acid}} Ca7Fe3(PO4)6(OH)2 + 6KOH + 12H2O + 9Cl^-$$

During synthesis of 30% IDANPs with 1× citrate, a 500 mL flask held at 25° C. was filled with 200 mL deionized water and stirred by stir bar as the following reagents were added in the order listed:

0.260 g Calcium Hydroxide ($Ca(OH)_2$)

0.243 g Iron Chloride ($FeCl_3$)

0.263 g Citric Acid Anhydrous ($C_6H_7O_7$)

0.408 g monopotassium phosphate ($KH_2PO_4$) that was pre-dissolved in 50 mL deionized water is added dropwise over a period of 1 minute.

Figure 3:
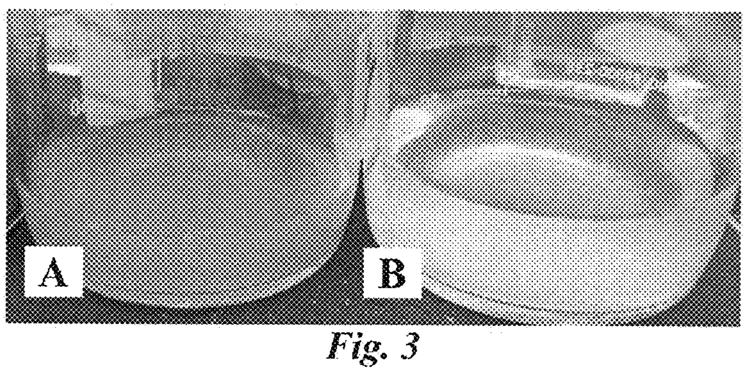
FIG. 3 A Pictures showing IDANPs synthesized at 25° C., with 30% iron-doping, and 5.5 mM citrate, B ANPs synthesized at 25° C., with 0% iron-doping, and 5.5 mM citrate.
Figure 4:
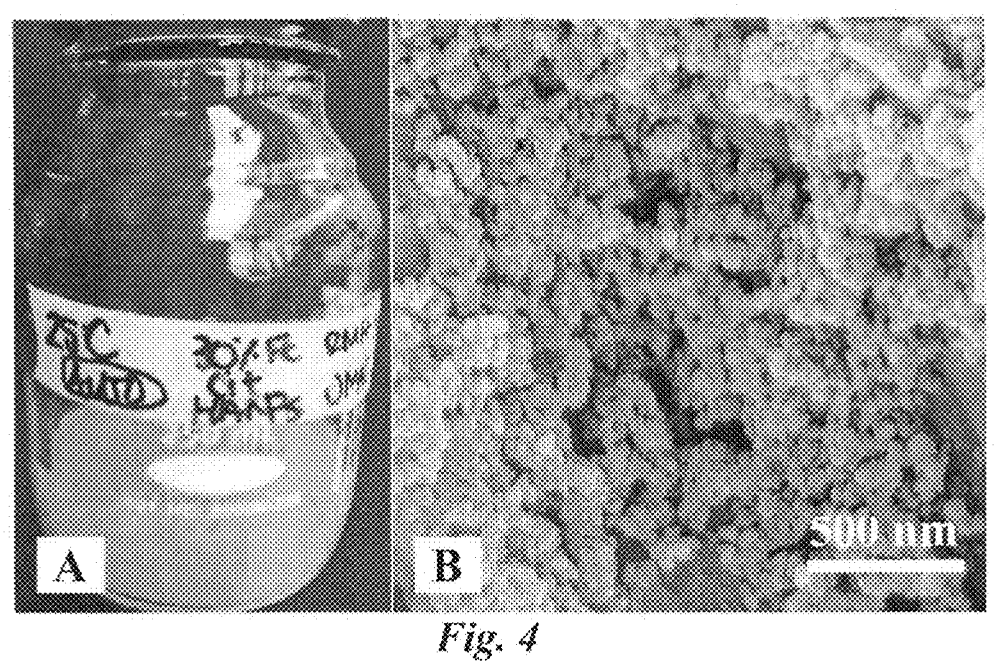
FIG. 4 IDANPs synthesized at 25° C. with 30% iron-doping and 5.5 mM citrate. A Picture of bulk IDANPs after synthesis. During synthesis, iron incorporation turns the IDANP-containing solution orange. B Scanning electron micrograph showing IDANPs after synthesis, which range from 20-50 nm in diameter and are approximately spherical (although amorphous) in shape.

The final solution was measured at a pH of approximately 4.5 and brought up to a pH of 7.5 using 1 M NaOH. IDANPs were then stirred at 25° C. for seven days. After seven days, IDANPs were centrifuged for 30 min at 2000 rpm. IDANP supernatant was then removed, leaving the IDANP pellet. The pellet was washed 2× with sterile, deionized water (18 Me), and IDANPs were re-suspended in deionized water before being sterilized in an autoclave for 40 minutes. IDANP concentration resulting from this synthesis procedure was estimated to be 1.54 mg/mL by simple drying method and weighing of dried IDANPs. The addition of iron results in the bulk colloid solution appearing orange in color (FIG. 3, FIG. 4A). In this embodiment, IDANPs are approximately 20-50 nm in diameter once synthesis is completed (FIG. 4B); however, it is contemplated that IDANPs with diameters within the range of 1-100 nm could be synthesized and used as described herein.

Plaque Assay.

Figure 5:
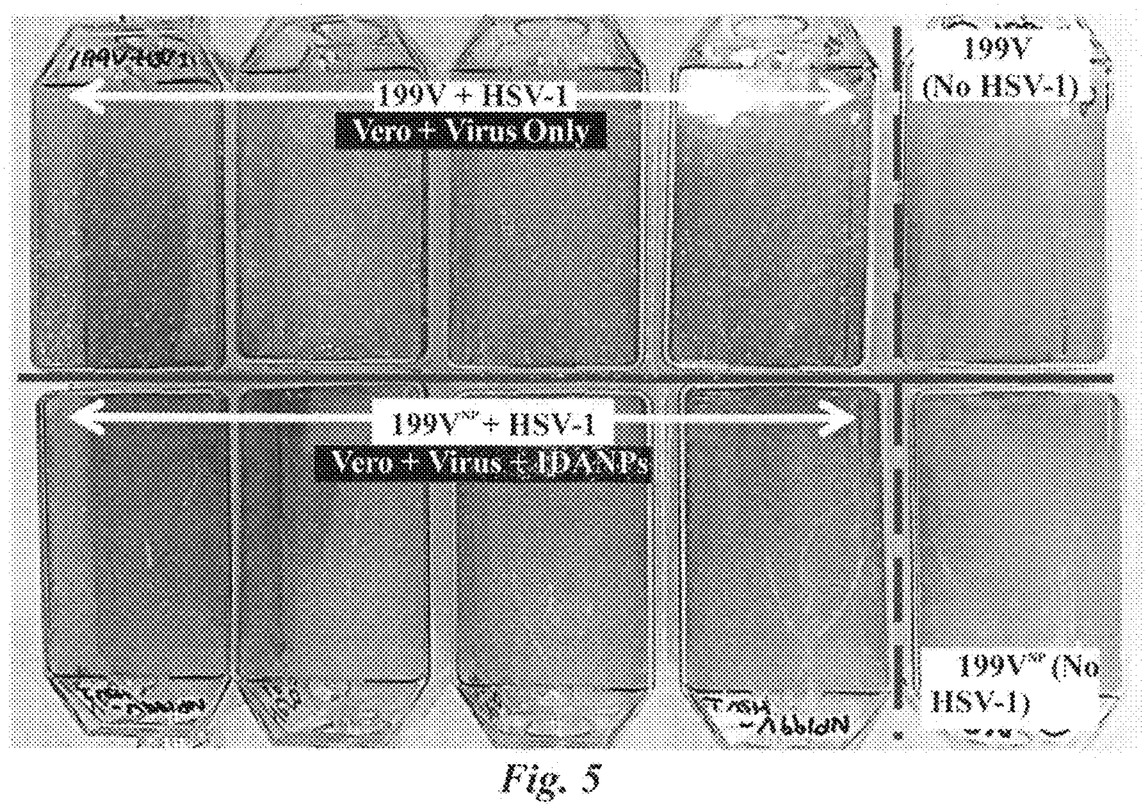
FIG. 5 Plaque assay results from a single experiment using Vero cells. Flasks on the top row (with exception of the far-right flask) were infected with HSV-1 in 199V media. Flasks on the bottom row (with exception of the far-right flask) were infected with HSV-1 in $199V^{NP}$ media. Results of three plaque assay experiments each containing four to seven pseudo-replicates per treatment showed an average decrease in HSV-1 infection of Vero cell monolayers of 84% when HSV-1 infection was carried out in 199V media with suspended IDANPs as compared to 199V alone ($p<0.001$). Negative controls containing 199V or $199V^{NP}$ without HSV-1 were also used to confirm plaque formation was due to HSV-1 infection (far right flasks on top and bottom rows).
Figure 6:
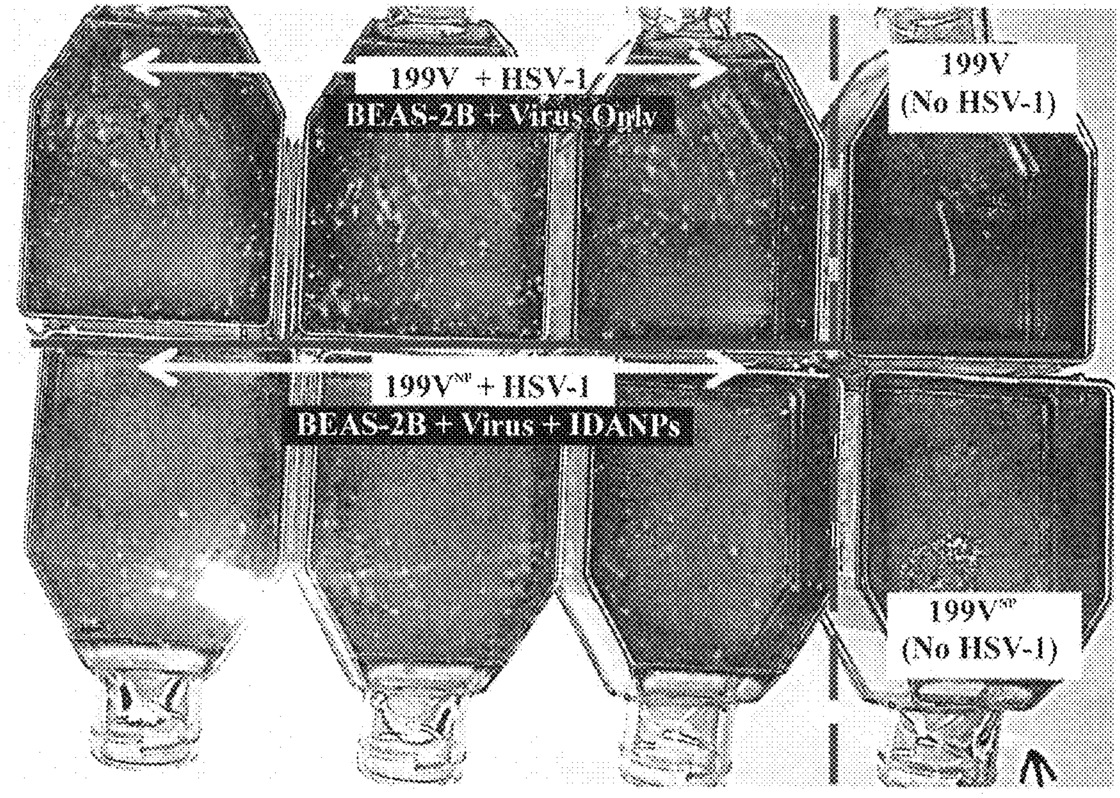
FIG. 6 Plaque assay results from a single experiment using BEAS-2B cells. Flasks on the top row (with exception of the far-right flask) were infected with HSV-1 in 199V media. Flasks on the bottom row (with exception of the far-right flask) were infected with HSV-1 in $199V^{NP}$ media. Results of three plaque assay experiments each containing 3-7 pseudo-replicates per treatment showed an average decrease in HSV-1 infection of BEAS-2B cell monolayers of 71% when HSV-1 infection was carried out in 199V media with suspended IDANPs ($199V^{NP}$) as compared to 199V alone. Negative controls containing 199V or $199V^{NP}$ without HSV-1 were also used to confirm plaque formation was due to HSV-1 infection (far right flasks on top and bottom rows).
Figure 7:
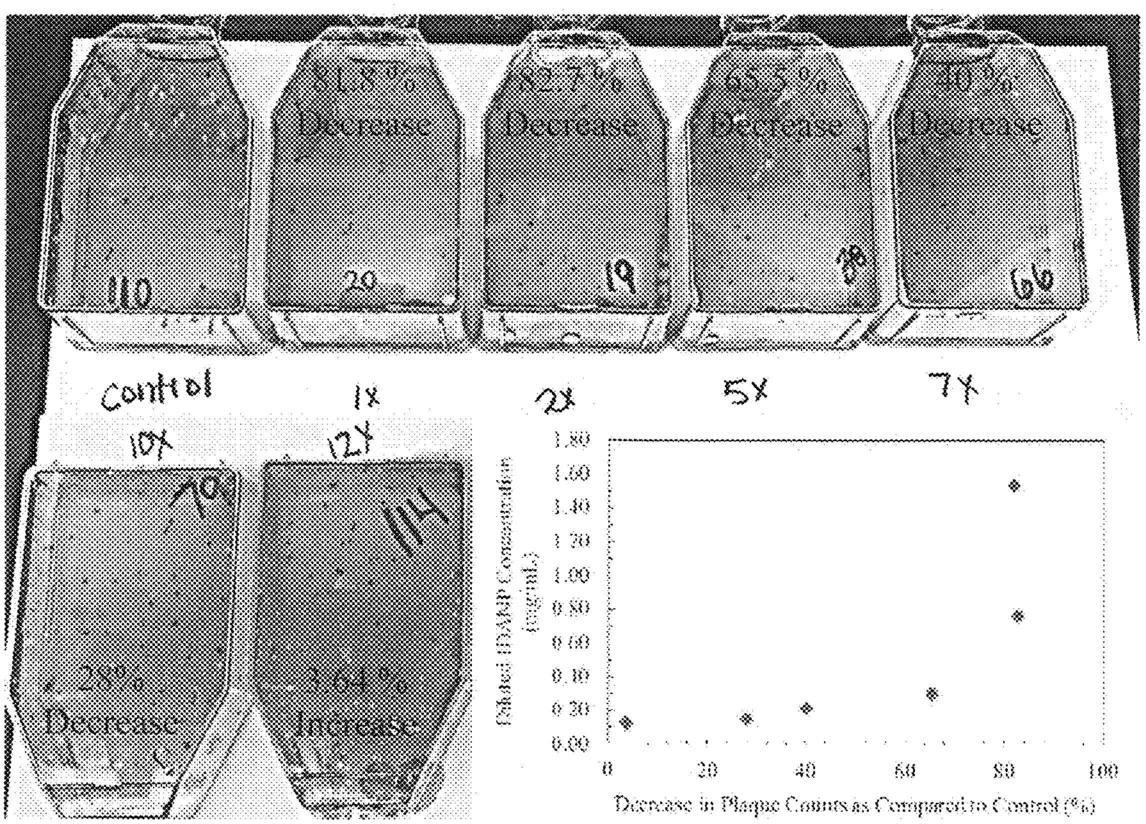
FIG. 7 Plaque assay results showing IDANPs diluted 10× (to 0.154 mg/mL) in 199V media still influence a 28% decrease in HSV-1 infection of BEAS-2B cell monolayers. IDANPs diluted beyond 12× or more did not affect HSV-1 infection of BEAS-2B significantly as compared to the control.
Figure 8:
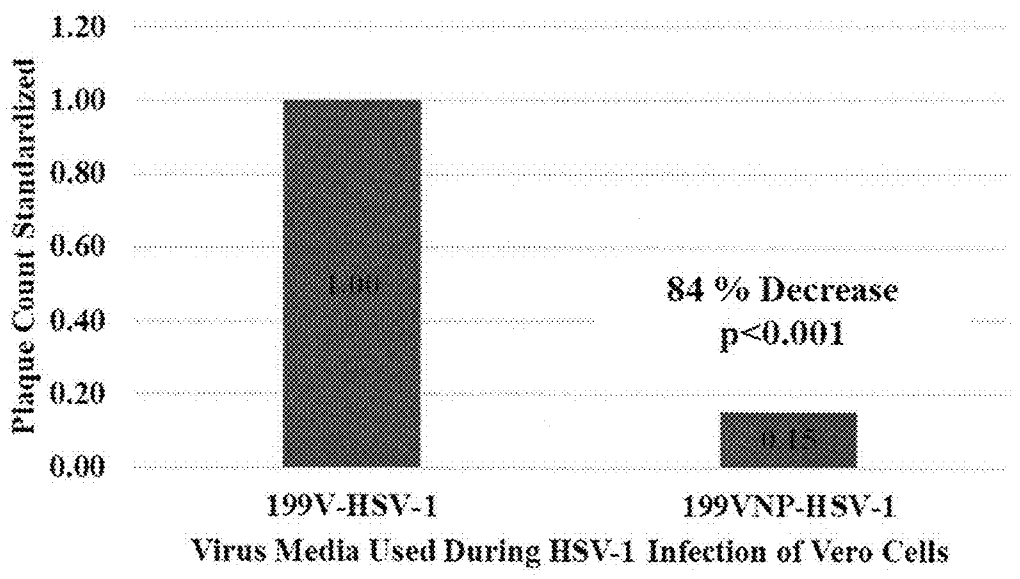
FIG. 8 Plaque assay results standardized from three plaque assay experiments using Vero cells. When HSV-1 infection was carried out in $199V^{NP}$ media, an 84% reduction of infection was observed, as compared to 199V media alone ($p<0.001$). Statistics were evaluated in SigmaPlot using a one-way ANOVA (V.11).
Figure 9:
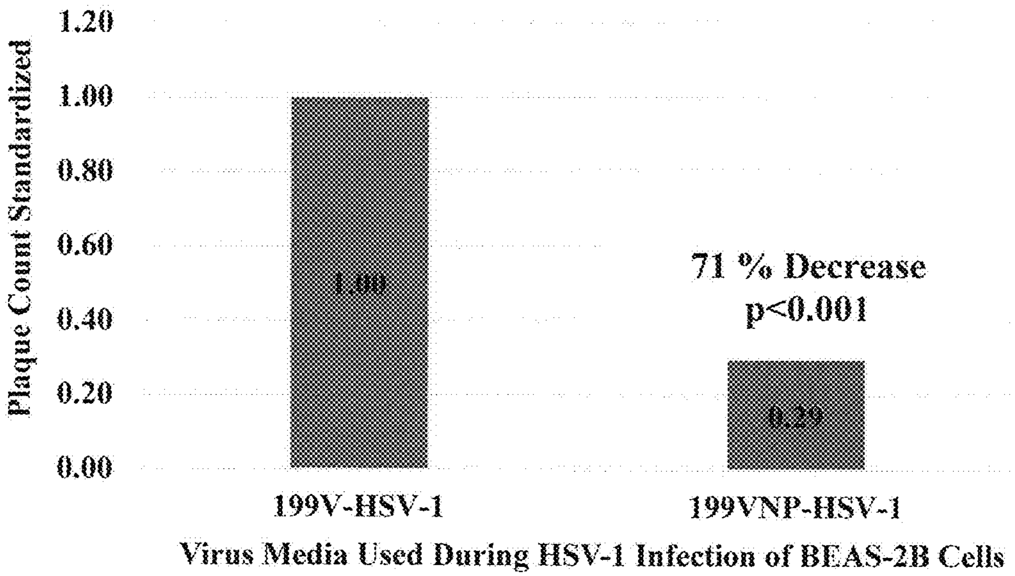
FIG. 9 Plaque assay results standardized from three plaque assay experiments using BEAS-2B cells. When HSV-1 infection was carried out in $199V^{NP}$ media, a 71% reduction of infection was observed, as compared to 199V media alone ($p<0.001$). Statistics were evaluated in SigmaPlot using a one-way ANOVA (V.11).

Plaque assay methods were adapted and modified from (Blaho et al., *Current Protocols in Microbiology,* 2005). When confluent, Vero or BEAS-2B cells maintained in 75 $cm^2$ flasks were lifted with trypsin (0.25%)-EDTA and split into 25 $cm^2$ flasks (15-17,000 cells per flask counted directly by hemocytometer) for plaque assay. In 25 $cm^2$ flasks, Vero and BEAS-2B cells were grown in MEM with 5% FBS and 1% P-S for 3-4 days, or until confluent. On the day of plaque assay, HSV-1 was removed from −80° C. freezer and thawed in the biosafety hood. Once thawed completely, HSV-1 was diluted into 199V media (Blaho et al., *Current Protocols in Microbiology,* 2005), or 199V with suspended IDANPs (1.54 mg/mL) to a pre-determined concentration for countable plaques (~50-100 PFUs/mL). To prepare 199V media with suspended IDANPs ($199V^{NP}$), IDANPs were centrifuged and supernatant removed before IDANPs were re-suspended in 199V. Growth media was then aspirated from 25 $cm^2$ flasks and replaced with 1 mL of HSV-1 in 199V or HSV-1 in $199V^{NP}$. HSV-1 was allowed to absorb to the cells for 2 hr in an incubator (37° C., 5% CO2) with gentle rocking every 30 min. After the 2 hr adsorption period, 199V or $199V^{NP}$ was removed from the flasks and replaced with 3 mL MEM with 7.5 μg/mL pooled human immunoglobulin (IgG). Flasks were then incubated for 3 days at 37° C. with 5% $CO_2$. After 3 days, media was removed from the 25 $cm^2$ flasks. To each flask, 1 mL methanol was added 5 min. After 5 min, methanol was removed from the flasks and replaced with 2 mL KaryoMax Giemsa Stain (diluted 1:10 with distilled water). Cell monolayers were stained for 20 min before the stain was removed and cell monolayers were rinsed with deionized water. Plaques were subsequently enumerated. Plaque assay was repeated in three separate experiments, with four, five, and seven pseudo-replicates per treatment condition for Vero cell line, and three, six, and seven for the BEAS-2B cell line. Negative controls were performed in all experiments, in which 199V or $199V^{NP}$ without HSV-1 were exposed to the cell lines during the 2 hr infection period. Results of plaque assays showed IDANPs influenced an 84% decrease in HSV-1 infection of Vero cells (FIG. 5), and a 71% decrease in HSV-1 infection of BEAS-2B cells (FIG. 6). Diluted to 10×, IDANPs still influenced a 28% decrease in HSV-1 infection of BEAS-2B cells (FIG. 7). Results of plaque assay experiments were standardized by dividing each $199V^{NP}$-HSV-1 treated flask plaque count by the average control (199V-HSV-1) plaque count value for that particular plaque assay (FIG. 8, FIG. 9). Statistics were evaluated in SigmaPlot V.11 using a one-way ANOVA.

LDH Cytotoxicity Assay.

For LDH cytotoxicity assay, Vero, BEAS-2B, or HeLa confluent cell cultures were lifted from 75 $cm^2$ flasks with 5 mL trypsin (0.25%)-EDTA before being pelleted by centrifugation (3000 rpm, 5 min) and trypsin subsequently replaced with MEM (10% FBS, 1% P-S). Cells were counted directly by hemocytometer and plated in a 96-well plate (7,000-9,000 cells per well) in 100 μL MEM (10% FBS, 1% P-S) and grown to confluence over the next 1-2 days. After cells were confluent, MEM was removed from the wells and replaced with either: (1) fresh MEM (10 wells), (2) fresh MEM with suspended IDANPs (25° C., 30% Fe, 5.5 mM citrate at 1.54 mg/mL, 10 wells), or DPBS (2 wells) as a vehicle control. Treatments were applied to the cell monolayers for 24 hr. Approximately 1 hr before the end of treatment time, cytotoxicity kit reagents were prepared according to protocols distributed by Biovision for Colorimetric Assay II (Documentation can be found at: https://wvvw.biovision.com/documentation/datasheets/K313.pdf). Approximately 15 min before the end of treatment time, 10 μL of prepared cell lysis solution was added to 5 of the MEM-only wells and pipetted up and down. The 5 wells inoculated with cell lysis solution constituted the high control for LDH cytotoxicity evaluation. After treatment time, solution from each of the wells was collected and placed in microcentrifuge tubes. Microcentrifuge tubes were spun at 600 rgf for 5 min to pellet any large cell components and IDANPs. After centrifugation, 10 μL from each microcentrifuge tube was transferred to individual wells in a fresh 96-well plate. To each well, 100 μl LDH Reaction Mix was added, pipetted up and down to mix, and incubated (37° C.) in the UV-Vis spectrometer for 1 hr 15 min with constant monitoring every 3 min at 450 nm. Biovision protocols indicated the reading should be taken when the high control was ~2.0 and the low control was <0.8. Wells with cell monolayers treated with NPs were repeated in 10 wells, low and high controls were repeated in five replicate wells each, and vehicle controls were performed in duplicate. Reference was taken after analysis period by taking additional readings at 450 nm and 620 nm simultaneously. Cytotoxicity (%) was determined by the following formula provided by Biovision (https://www.biovision.com/documentation/datasheets/K313.pdf):

$$\text{Cytotoxicity (\%)} = \left[\frac{(\text{Test Sample} - \text{Low Control})}{(\text{High Control} - \text{Low Control})}\right] \times 100\%$$

Using cytotoxicity (%), it was determined that IDANPs posed 0.00% cytotoxicity to BEAS-2B and HeLa cell lines, and 4.27% cytotoxicity to the Vero cell line.

XTT Cytotoxicity Assay.

Figure 10:
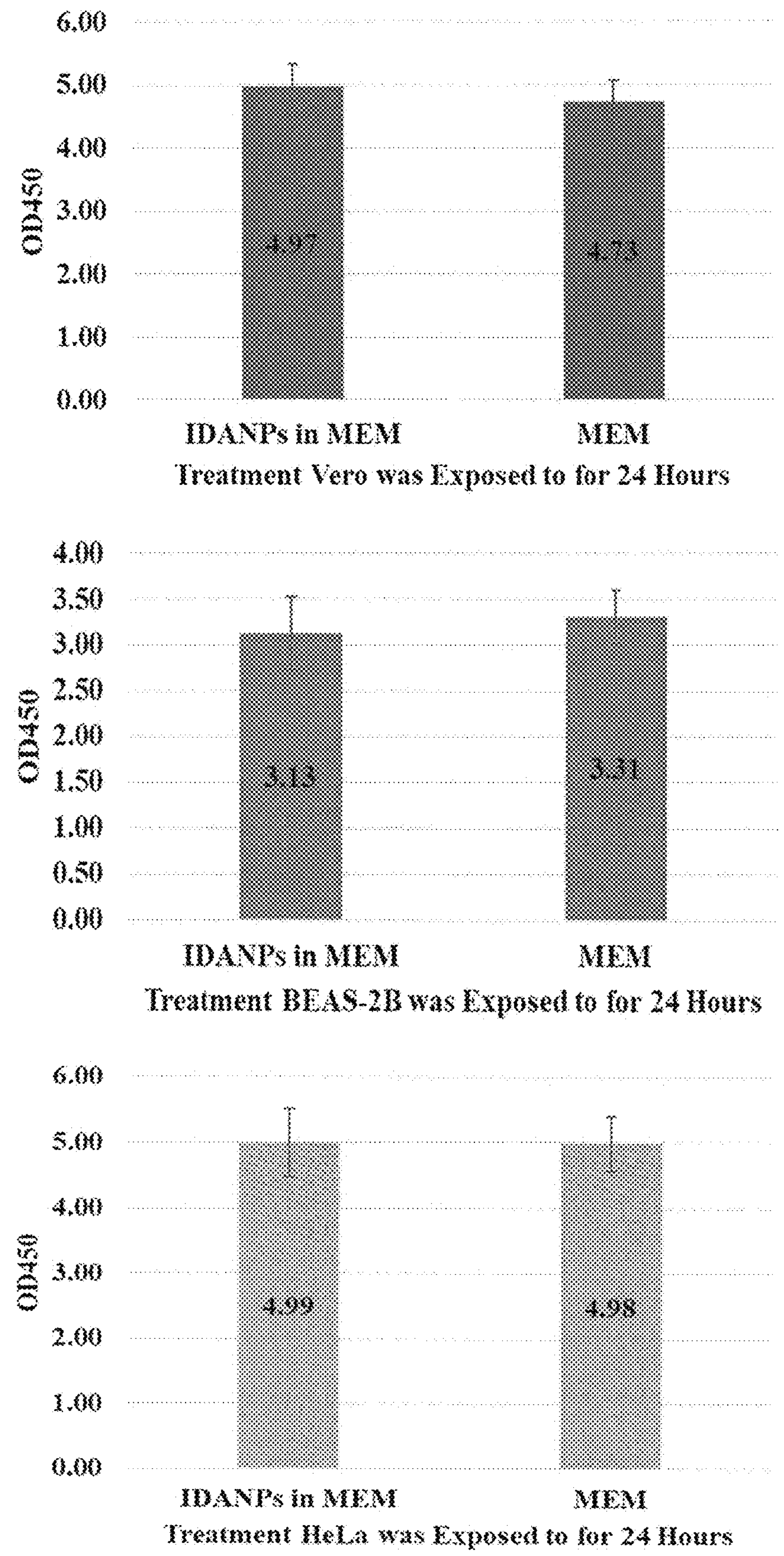
FIG. 10 Results from XTT cytotoxicity assays performed with MEM versus MEM with suspended IDANPs. Results show that in Vero ($p=0.276$), BEAS-2B ($p=0.131$), and HeLa ($p=0.960$) cell lines, no significant decrease in enzyme activity is imposed when cell monolayers are exposed to IDANPs for 24 hr. Statistics were evaluated in SigmaPlot using a one-way ANOVA (V.11). Error bars extend one standard deviation above and below the mean.

Vero, BEAS-2B, and HeLa confluent cell cultures were lifted from 75 $cm^2$ flasks with 5 mL trypsin (0.25%)-EDTA before being pelleted by centrifugation (3000 rpm, 5 min), and trypsin was subsequently replaced with MEM (10% FBS, 1% P-S). Cells were counted directly by hemocytometer and plated in a 96-well plate (7,000-9,000 cells per well) in 100 μL MEM (10% FBS, 1% P-S) and grown to confluence over the next 1-2 days. After cells were confluent, MEM was removed from the wells and replaced with either: (1) fresh MEM (11 wells), (2) fresh MEM with suspended IDANPs (25° C., 30% Fe, 5.5 mM citrate at 1.54 mg/mL, 11 wells), DPBS (2 wells) as a vehicle control. Treatments were applied to cell monolayers for 24 hr. During the last hour of exposure to the treatments, XTT was dissolved 0.01 g into 10 mL DPBS, and phenazine methosulfate (PMS) was dissolved 0.05 g into 1 mL sterile, deionized water (18MΩ). Then, 100 μL PMS solution was pipetted into 5 mL of the XTT solution. During preparation, all of these solutions were kept on ice. In addition, 10 μL cell lysis solution was added to one well containing MEM only, and one well containing MEM with suspended IDANPs as dead controls. At the conclusion of treatment, all solution was removed from the wells, cell monolayers were washed 2× with DPBS, and replaced with fresh MEM. This wash/replacement procedure was used to eliminate any signal coming from XTT interacting with IDANPs or IDANPs alone. Each well was subsequently inoculated with 100 μL XTT/PMS solution, and plates were placed back into the incubator for 2 hrs, with final absorption read at 450 nm (reference at 620 nm). During these studies, 10 replicate wells were treated with MEM only, 10 with MEM with suspended IDANPs, 2 dead controls (one per MEM or MEM with IDANPs) were used, as well as 2 vehicle controls (treated with DPBS). Statistics were evaluated in SigmaPlot using a one way ANOVA V.11, and it was determined that no significant difference in mitochondrial enzyme activity occurred between Vero ($p=0.276$), BEAS-2B ($p=0.131$), or HeLa ($p=0.960$) cells which had or had not been exposed to IDANPs (FIG. 10).

Plaque Assay: IDANP Influence Over HSV-1 Infection of Vero Cell Line.

In plaque assays, HSV-1 infection of Vero cells was carried out in 199V viral media (Blaho et al., *Current Protocols in Microbiology,* 2005) with ($199V^{NP}$) or without (199V) suspended IDANPs. Three separate plaque assay experiments were performed, with 4, 5, and 7 pseudo-replicates per experimental treatment (199V or $199V^{NP}$), as well as 2 negative control flasks which contained 199V or $199V^{NP}$ without HSV-1. Results from the three plaque assays were standardized by dividing each $199V^{NP}$-HSV-1 plaque count with the average control (199V-HSV-1) plaque count for that particular plaque assay. When summarized, results show an 84% decrease in plaques ($p<0.001$) from Vero cell monolayers treated with $199V^{NP}$-HSV-1 versus Vero cell monolayers treated with the control, 199V-HSV-1 (FIG. 8).

Plaque Assay: IDANP Influence Over HSV-1 Infection of BEAS-2B Cell Line.

In plaque assays, HSV-1 infection of BEAS-2B cells was carried out in 199V viral media (Blaho et al., *Current Protocols in Microbiology,* 2005) with ($199V^{NP}$) or without (199V) suspended IDANPs. Three separate plaque assay experiments were performed, with 3, 6, and 7 pseudo-replicates per experimental treatment (199V or $199V^{NP}$), as well as 2 negative control flasks which contained 199V or $199V^{NP}$ without HSV-1. Results from the three plaque assays were standardized by dividing each $199V^{NP}$-HSV-1 plaque count with the average control (199V-HSV-1) plaque count for that particular plaque assay. When summarized, results show a 71% decrease in plaques ($p<0.001$) from BEAS-2B cell monolayers treated with $199V^{NP}$-HSV-1 versus Vero cell monolayers treated with the control, 199V-HSV-1 (FIG. 9). Additional plaque assays were also performed to determine if lower dosage of IDANP could be used to still effectively prevent HSV-1 infection of BEAS-2B cells. Plaque assay results showed IDANPs diluted 10× (to 0.154 mg/mL) in 199V media still influenced a 28% decrease in HSV-1 infection of BEAS-2B cell monolayers. IDANPs diluted beyond 12× or more did not affect HSV-1 infection of BEAS-2B as compared to the control (FIG. 7).

LDH Cytotoxicity Assays: Cytotoxicity Posed by IDANPs in Vero, BEAS-2B, and HeLa Cell Lines.

LDH cytotoxicity assay performed included a 24 hr. exposure period, in which IDANPs were exposed to Vero, BEAS-2B, or HeLa cell monolayers in the same concentration as was delivered during plaque assay experiments (1.54 mg/mL). IDANPs imposed 4.27% cytotoxicity in the Vero cell line, and 0.00% cytotoxicity in the BEAS-2B and HeLa cell lines.

XTT Cytotoxicity Assays: Cytotoxicity Posed by IDANPs in Vero, BEAS-2B, and HeLa Cell Lines.

LDH cytotoxicity assay performed included a 24 hr. exposure period, in which, IDANPs suspended in MEM (10% FBS, 1% P-S) were exposed to Vero, BEAS-2B, or HeLa cell monolayers in the same concentration as was delivered during plaque assay experiments (1.54 mg/mL). In all cases, IDANPs did not cause statistically significant decreases in enzyme activity in Vero, BEAS-2B, or HeLa cell lines (FIG. 10). Statistics were evaluated in SigmaPlot V.11 using a one-way ANOVA. Listed are the corresponding p-values for each XTT experiment comparing mammalian cell lines exposed or not exposed to IDANPs: Vero ($p=0.276$), BEAS-2B (0.131), and HeLa ($p=0.960$).

IDANPs have demonstrated a unique influence over phage infection and killing of bacteria cells, in which IDANP-exposed bacterial cultures experience up to 2× the bacterial death as compared to controls (Andriolo et al., *Journal of Vacuum Science and Technology B,* 2013). As antibacterial resistance to mainstream antibiotics increases (Centers for Disease Control and Prevention, 2013), phage have been suggested as an alternative antibiotic therapy. IDANPs are composed of HA, a material found in mammalian bones and teeth and used in many FDA approved medical applications (Palmer et al., *Chemical Reviews,* 2008 & Hench, *Journal of the American Ceramic Society,* 1998). The potential biocompatibility of IDANP's, coupled with the functionality of these NPs as an aid to an alternative antibiotic therapy, make them of interest for medical applications. Here, IDANPs were examined in mammalian systems to ensure IDANP adjuvants used to increase phage infection of bacteria would not also increase mammalian viral infection in a mammalian system. Results of plaque assay studies in both Vero and BEAS-2B cell lines show that IDANPs, do not increase HSV-1 infection, but rather decrease HSV-1 infection of Vero cells by 84% and BEAS-2B cells by 71%. The observed therapeutic potential of IDANPs as an antiviral garnered from our plaque assay studies prompted a cytotoxicity evaluation of IDANPs using LDH and XTT cytotoxicity assays in Vero, BEAS-2B, and HeLa cell lines. Cytotoxicity results show IDANPs are largely non-toxic to Vero, BEAS-2B, and HeLa cell lines. Previous work has shown iron(III) inactivates HSV-1 (Sagripanti et al., *Applied and Environmental Microbiology,* 1993), and in more recent studies, it has been shown that iron(III) inhibits replication of DNA and RNA viruses (Terpilowska et al., *Biometals,* 2017). However, in the latter publication (Terpilowska et al., *Biometals,* 2017), a MTT cytotoxicity evaluation is provided, which shows that at approximately 150 μM (as is found in IDANPs), iron caused a reduction in cell viability of HEp-2 (HeLa contaminant) cells to ~73% (Terpilowska et al., *Biometals,* 2017). For comparison, at the same concentration, IDANPs maintain 100% cell viability at 150 μM in Vero and HeLa cell lines, and 94.6% in the BEAS-2B cell line. These findings suggest that the HA matrix of the IDANP provides a biocompatible method/mechanism for iron delivery, and that IDANPs act as an effective and safe anti-viral agent.

As such, compositions and methods of using IDANPs for the prevention, treatment, or alleviation of signs or symptoms associated with viral activation or infection are disclosed herein. In one embodiment, IDANPs are suspended in any medium suitable for therapeutic delivery to virus infected or affected cells. One exemplary embodiment includes suspension of IDANPs in a semi-solid medium capable of direct application to virus infected or affected tissue, such as lips, similar to how chap stick is applied. Other exemplary embodiments include IDANPs suspended in medium consisting of one of the following: solid, semi-solid, Newtonian or Non-Newtonian fluid, or powder.

IDANP compositions used for prevention, treatment, or alleviation of signs or symptoms associated with viral activation or infection are prepared as follows: IDANPs are synthesized as stated herein (see [0007] and [0026]). In one embodiment, supernatant created during IDANP synthesis/preparation is removed by centrifugation of the particles and removal of supernatant by pipette. IDANPs without supernatant are then suspended by any suitable means into any medium suitable for therapeutic delivery to virus infected or affected cells. In this embodiment, suspending the IDANPs is accomplished by mixing IDANPs into the selected media by stir bar on a stir plate, or vortexing. One skilled in the art would recognize that various suspension means could be utilized to prepare IDANPs for delivery.

Once the IDANPs are suspended in the selected medium, the medium is delivered to the virus affected or infected cells by any accepted therapeutic means. One skilled in the art would recognize that such compositions could be delivered by various therapeutic means including, but not limited to injection, oral administration, or direct application. In an exemplary embodiment, the semi-solid IDANP medium would be delivered by direct application to the lips, similar to the application of chap stick, to treat signs or symptoms associated with viral activation or infection.

It is understood that the foregoing specific examples are merely illustrative of the present invention. Certain modifications of the compositions and/or methods may be made and still achieve the objectives of the invention. Such modifications are contemplated within the scope of the claimed invention.

What is claimed is:

1. A method of decreasing viral infection of mammalian cells comprising:

a. providing citrate functionalized iron-doped apatite nanoparticles (IDANPs);

b. suspending said IDANPs in a medium; and c. delivering said IDANP medium to virus affected or infected mammalian cells.

2. The method of claim 1 where said virus is comprised of a mammalian virus.

3. The method of claim 2 where said mammalian virus is further comprised of a DNA containing virus.

4. The method of claim 2 where said mammalian virus is further comprised of a RNA containing virus.

5. The method of claim 1 where said virus is comprised of herpes simplex virus 1 (HSV-1).

6. The method of claim 1 where said IDANPs are comprised of 30% iron doping.

7. The method of claim 1 where said medium is selected from the group consisting of: solid, semi-solid, Newtonian fluid, Non-Newtonian fluid, or powder.

8. The method of claim 1 where the delivering step is selected from the group consisting of injection, oral administration, absorption, or direct application.

9. The method of claim 1, wherein the IDANPs are sized from 1-100 nm in diameter.

10. The method of claim 9, wherein the IDANPs are sized from approximately 20-50 nm in diameter.

11. The method of claim 1, wherein the apatite in the IDANPs is hydroxyapatite.

12. The method of claim 1, wherein the mammalian cells are selected from the group consisting of Vero cells, BEAS-2B cells, and HeLa cells.

13. The method of claim 1, wherein the iron in the IDANPs is iron (III).

* * * * *